(12) United States Patent
Luizzi

(10) Patent No.: US 7,611,501 B2
(45) Date of Patent: Nov. 3, 2009

(54) SANITARY NAPKIN INCLUDING BODY-FACING ADHESIVE

(75) Inventor: Joseph M. Luizzi, Newtown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 11/263,494

(22) Filed: Oct. 31, 2005

(65) Prior Publication Data

US 2007/0100313 A1 May 3, 2007

(51) Int. Cl.
*A61F 13/15* (2006.01)
(52) U.S. Cl. ............. 604/385.03; 604/387; 604/385.05; 604/389; 604/386
(58) Field of Classification Search ............ 604/385.03, 604/378, 386, 387, 365, 366, 385.05, 389
See application file for complete search history.

(56) References Cited

U.S. PATENT DOCUMENTS

| 4,555,430 A | 11/1985 | Mays |
| 5,916,670 A | 6/1999 | Tan et al. |
| 6,191,189 B1 | 2/2001 | Cinelli et al. |
| 6,213,993 B1 | 4/2001 | Zacharias et al. |
| 6,316,524 B1 | 11/2001 | Corzani et al. |
| 6,620,143 B1 | 9/2003 | Zacharias et al. |
| 2003/0208112 A1 | 11/2003 | Schmidt et al. |

FOREIGN PATENT DOCUMENTS

| EP | 1637106 A2 | 3/2006 |
| GB | 2 284 767 A | 6/1995 |
| WO | WO 00/24350 A1 | 5/2000 |

OTHER PUBLICATIONS

European Search Report EP 06 25 5585 dated Feb. 21, 2007.

*Primary Examiner*—Jacqueline F. Stephens

(57) ABSTRACT

An absorbent article including an adhesive on a body-facing surface of the article for securing the article to the body, the adhesive having the following properties: $G'_{[100\ rad/sec\ @\ 37°\ C.]}/G'_{[0.1\ rad/sec\ @\ 37°\ C.]} \geq 4.5$; and $-20°\ C. \leq Tg(°\ C.) \leq 15°\ C.$

28 Claims, 4 Drawing Sheets

FIG. 3
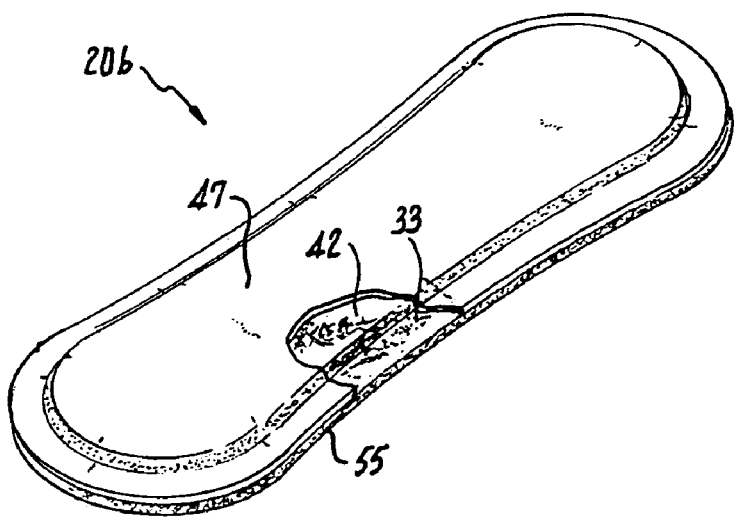
FIG. 4
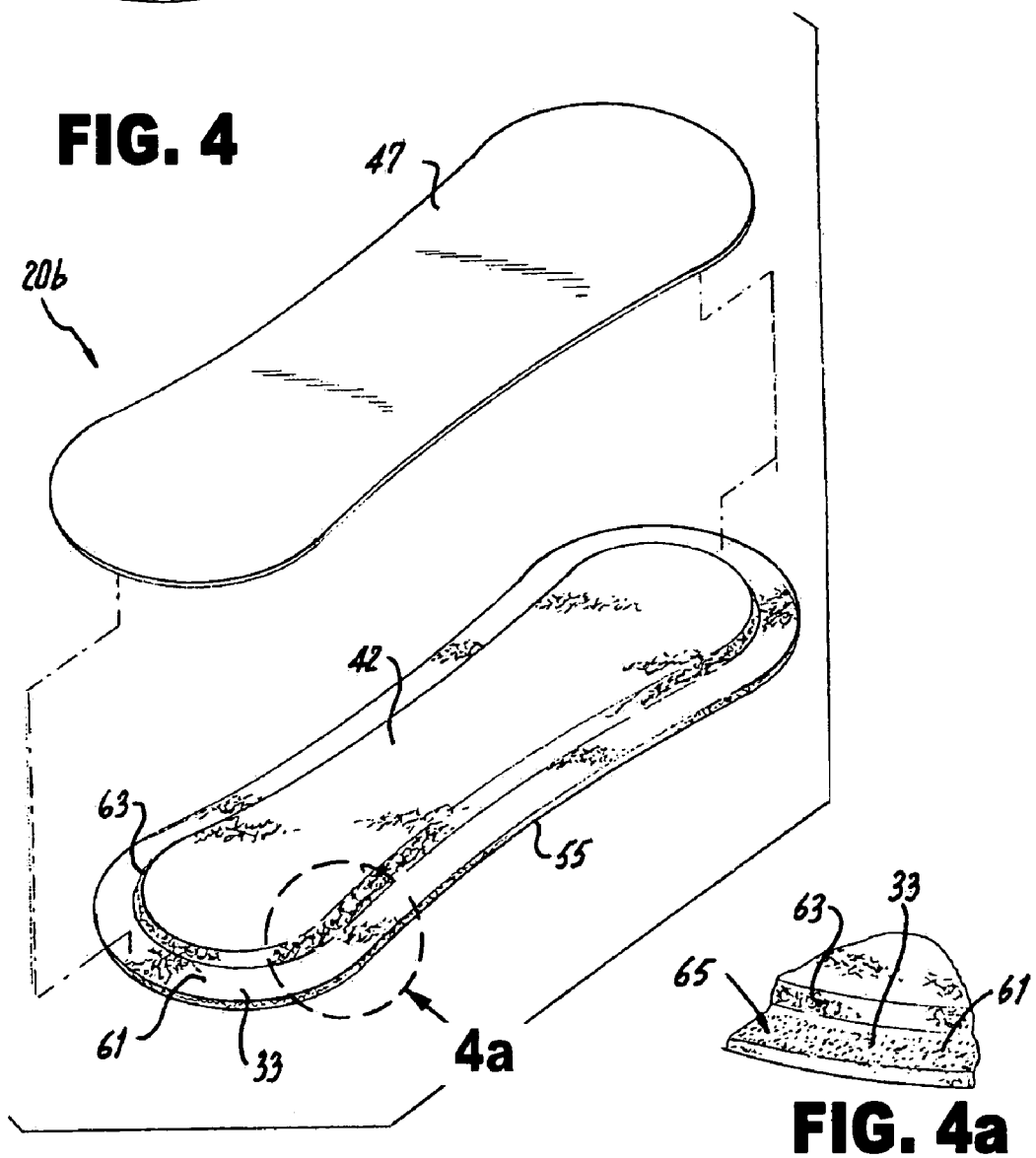
FIG. 4a

ND BODY-FACING ADHESIVE

SANITARY NAPKIN INCLUDING BODY-FACING ADHESIVE

FIELD OF THE INVENTION

The present invention relates to a body attachable sanitary protection article, such as a sanitary napkin, and in particular a sanitary napkin including an adhesive on a body-facing surface of the napkin for comfortably and securely attaching the napkin to the body.

BACKGROUND OF THE INVENTION

Various absorbent articles configured to be arranged adjacent the body to absorb body fluids such as menses, urine and the like are well known. With respect to feminine hygiene, napkins and liners have been developed for external use about the pudendal region of a female.

Securement of a sanitary napkin or liner during use is normally accomplished by attaching the sanitary garment by pressure sensitive adhesive to the wearer's undergarment. Napkins having wings or flaps that fold over the edges of the garment and are attached to the underside of the garment using an adhesive are also known.

The prior art also teaches sanitary protection articles that are intended to be secured directly to the body by an adhesive arranged on a body-facing surface of the article. For example, GB2284767A purports to disclose an absorbent article including an absorbent and an adhesive arranged adjacent the absorbent, the adhesive being designed to contact the wearer's body during use.

A problem with body attachable sanitary articles of the type discussed above is that they must adhere securely to the body during use yet at the same time be selectively detachable from the skin without causing pain to the user. Attempts have been in the prior art to solve this problem. For example, U.S. Pat. Nos. 6,620,143 and 6,213,993 purport to disclose body-attachable sanitary napkins including adhesives that permit the napkin to be comfortably worn and removed with little or no pain to the wearer. Similarly, U.S. Pat. No. 6,191,189 purports to disclose a substrate and adhesive combination that provides secure attachment and is pleasing to the skin upon application, yet causes no discomfort upon removal.

Despite the above described efforts, there is still a need for body attachable absorbent articles that remain securely attached to the body during use yet at the same time permit the user to selectively attach and remove the article with little or no pain.

SUMMARY OF THE INVENTION

According to one aspect of the invention, the present invention provides a body-attachable absorbent article including a body-facing surface, a garment-facing surface, an adhesive applied to said body-facing surface for selectively securing the article to a body of a user, wherein said adhesive has the following properties:

$G'_{[100\ rad/sec@\ 37°\ C.]}/G'_{[0.1\ rad/sec@\ 37°\ C.]} \geq 4.5$; and $-20°\ C. \leq Tg(°\ C.) \leq 15°\ C.$ According to another aspect of the invention, the present invention provides a body-attachable sanitary napkin including a cover layer, a barrier layer, an absorbent layer arranged between the cover layer and the barrier layer, an adhesive applied to a body-facing surface of the napkin for selectively securing the article to a body of a user, wherein said adhesive has the following properties:

$G'_{[100\ rad/sec@\ 37°\ C.]}/G'_{[0.1\ rad/sec@\ 37°\ C.]} \geq 4.5$; and $-20°\ C. \leq Tg(°\ C.) \leq 15°\ C.$ According to yet another aspect of the invention, the present invention provides a body-attachable absorbent article including a cover layer, a barrier layer, an absorbent layer arranged between the cover layer and the barrier layer, an adhesive applied to a body-facing surface of the napkin for selectively securing the article to a body of a user, wherein the adhesive has the following properties:

$G'_{[100\ rad/sec@\ 37°\ C.]}/G'_{[0.1\ rad/sec@\ 37°\ C.]}$ between 4.8 and 6; and a Tg value between $-20°$ C. and $-10°$ C.;

the article having an average removal force of between 3.0 g/per mm width of adhesive and 4.0 g/mm width of adhesive.

BRIEF DESCRIPTION OF THE DRAWINGS

Examples of embodiments of the present invention will now be described with reference to the drawings, in which:

FIG. 3 is a perspective view of a body attachable sanitary napkin according to another embodiment of the present invention, the release member thereof being partially broken away to show the cover layer;

FIG. 4 is a partially exploded perspective view of the sanitary napkin shown in FIG. 3; and FIG. 4a is a detailed perspective view of a portion of the sanitary napkin shown in FIGS. 3 and 4;

DETAILED DESCRIPTION OF THE INVENTION

The present invention relates to a disposable absorbent article including an adhesive on a body-facing surface thereof for securing the article to the body of a wearer. For simplicity of description only, the invention will be described as applied to a sanitary napkin, but the invention is not limited thereto. The present invention may also be applied to interlabial devices which reside partially within and partially outside the female wearer's vestibule as well as to other absorbent articles such as pantiliners, incontinence articles and the like.

Figure 1:
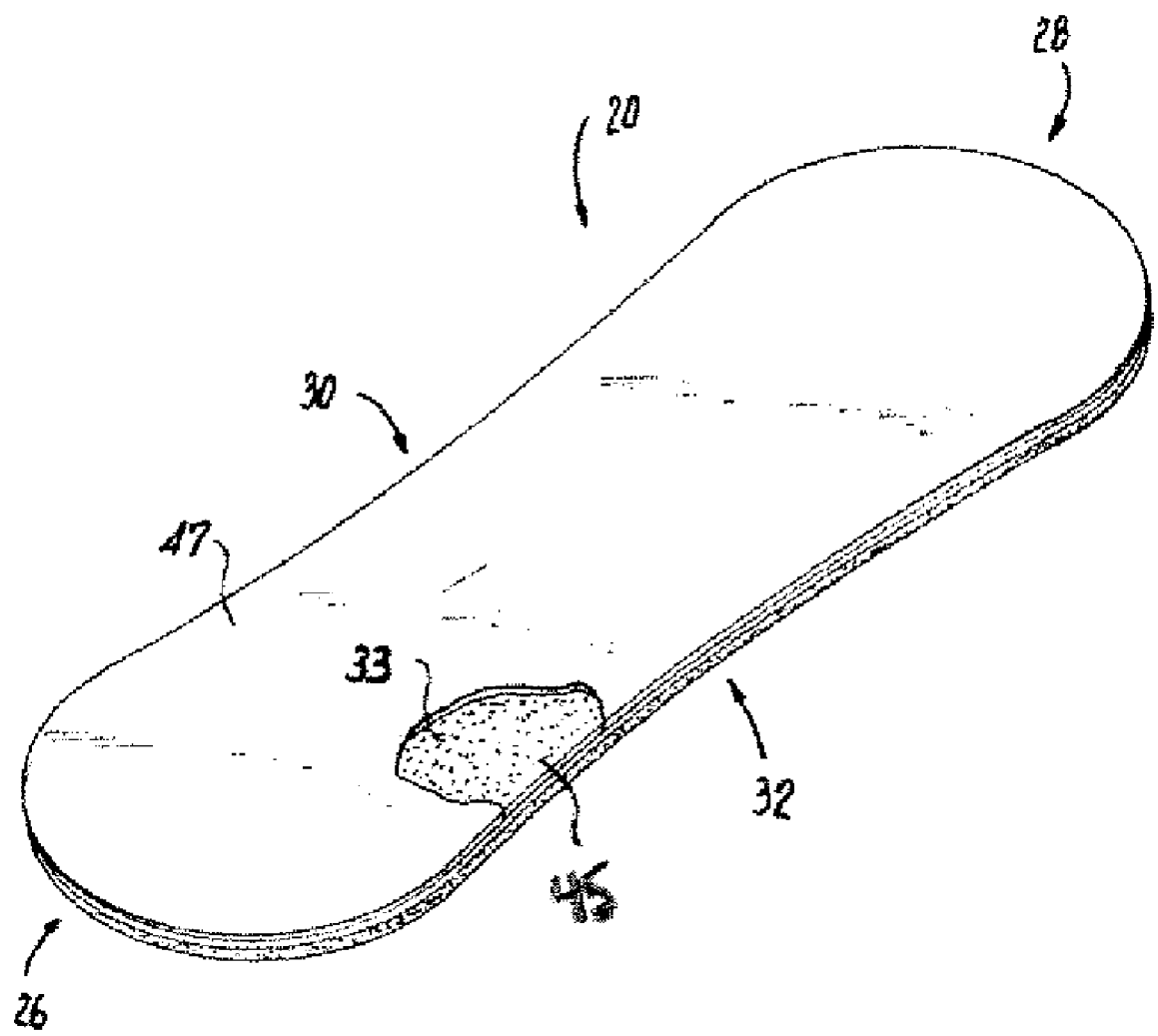
FIG. 1 is a perspective view of a body attachable sanitary napkin according to the present invention, the release member thereof being partially broken away to show the cover layer.
Figure 2:
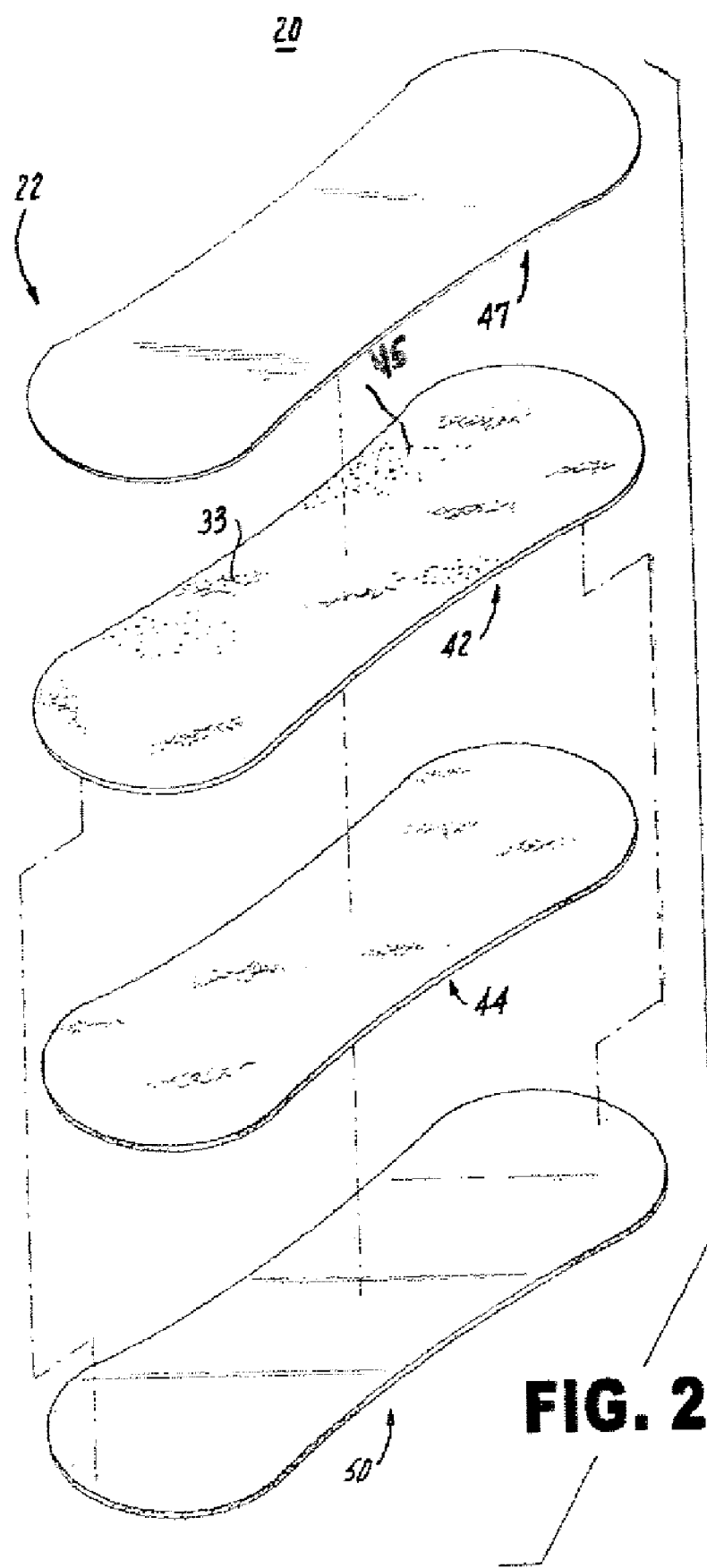
FIG. 2 is an exploded perspective view of the sanitary napkin shown in FIG. 1.

Referring to FIGS. 1 and 2, there is shown an embodiment of the present invention, a feminine sanitary napkin 20. The sanitary napkin 20 has a main body 22 with a first transverse side 26 defining a front portion thereof and a second transverse side 28 defining a rear portion thereof. The main body also has two longitudinal sides, namely a longitudinal side 30 and a longitudinal side 32.

As depicted in FIG. 2, the main body 22 is of a laminate construction and preferably comprises a fluid-permeable cover layer 42, an absorbent system 44 and a fluid-impervious barrier layer 50. The absorbent system 44 may comprise a single layer of material or may comprise multiple layers. For example, the absorbent system 44 may comprise a single layer core or it may include a transfer layer and a core.

In the embodiment of the invention shown in FIGS. 2 and 3, an adhesive 33 for securing the napkin 20 to the body of a user is applied to the body facing surface 45 of the cover 42. The adhesive 33 can be applied to the body facing surface 45 by any known technique in the art such as screen printing, extruding, spraying, or slot coating. The adhesive 33 may be applied uniformly over the body facing surface 45 in an amount of between about 35 gsm (g/m$^2$) to about 120 gsm, and more preferably between about 45 gsm to about 100 gsm. Alternatively, in one preferred embodiment of the present invention, the adhesive is applied in a plurality of distinct spaced lines or bands. For example, the adhesive may be applied in two or more spaced bands having a width of between about 3 mm and about 40 mm, and more preferably between about 10 mm and 25 mm. Each of the plurality of spaced adhesive bands may be spaced from each other by a distance between about 3 mm and about 60 mm apart, and more preferably between about 10 mm and about 25 mm apart. This distance between the adhesive bands is as measured from the longitudinal side edge (i.e. the side edge running in the length direction of the product) of one adhesive band to the adjacent side edge of the adjacent adhesive band. The adhesive is applied in an amount of between about 35 gsm (g/m$^2$) to about 120 gsm, and more preferably between about 45 gsm to about 100 gsm to form each of the adhesive bands or lines.

Prior to use of the article the adhesive 33 may be covered by a removable release member 47. The release member 47 preferably includes a release coating on the surface of the release member 47 that is in contact with the adhesive 33 to thereby facilitate the easy removal of the release member 47 prior to attachment of the napkin 20 to the body.

The release coating 49 may be a material based on polydimethylsiloxane chemistries, generically referred to as "silicones". The release coating 49 may also be a material based on other non-silicone chemistries, such as fluropolymers, alkyds, carbamates, urethanes, chromium complexes, acrylics, poly vinyl alcohols, or olefins.

Another embodiment of the present invention, a sanitary napkin 20b, is shown in FIGS. 3, 4 and 4a. In the sanitary napkin 20b the barrier layer 55 is dimensioned so a portion 61 thereof extends outward relative to an terminal edge 63 of the cover 42. The adhesive 33 for attaching the article to the body is applied to a body facing surface 65 of the barrier portion 61. In one embodiment of the invention the adhesive 33 is applied in a uniform manner to the body facing surface 65 of the barrier portion 61 in an amount of between about 35 gsm (g/m$^2$) to about 120 gsm, and more preferably between about 45 gsm to about 100 gsm. Alternatively, in one preferred embodiment of the present invention, the adhesive is applied in a plurality of distinct spaced lines or bands to the body facing surface 65 of the barrier portion 61.

The napkin 20b is provided with a removable release member 47 to cover the adhesive 33 prior to use. As shown in FIGS. 3 and 4, the release member 47 may be shaped such that it extends over the entire top surface of the cover 42 and barrier portion 61. Alternatively, the removable release member 47 may have a substantially oval shape (not shown) such that the release member 47 corresponds in shape to the barrier portion 61 and has a central open area (i.e. a central oval shaped through hole) that corresponds to the shape of the cover 42. In all other respects the embodiment of the invention shown in FIGS. 3, 4 and 4a is the same as the embodiment described above with reference to FIGS. 1-2.

Main Body—Cover Layer

The cover layer 42 may be a relatively low density, bulky, high-loft non-woven web material. The cover layer 42 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 42 has a basis weight in the range of about 10 gsm to about 75 gsm.

Bi-component fibers may be made up of a polyester layer and a an polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transport it away from the body and the point of deposition. Therefore, the cover layer contributes little to the time taken for the napkin to absorb a given quantity of liquid (penetration time).

Advantageously, the fibers which make up the cover layer 42 should not lose their physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the other layers of the absorbent system 44. Thus, the cover layer 42 is advantageously wettable, hydrophilic and porous. When composed of synthetic hydrophobic fibers such as polyester or bi-component fibers, the cover layer 42 may be treated with a surfactant to impart the desired degree of wettability.

In one preferred embodiment of the present invention the cover is made from a spunlace nonwoven material having from about 0 to about 100% polyester and from about 0 to about 100% rayon. The spunlace material may also be made from about 10% to about 65% rayon and from about 35% to about 90% polyester. In lieu of, and/or in combination with the polyester, polyethylene, polypropylene or cellulosic fiber may be used with the rayon. Optionally, the material used for the cover layer may include binders such as thermoplastic binders and latex binders.

Alternatively, the cover layer 42 can also be made of polymer film having large pores. Because of such high porosity, the film accomplishes the function of quickly transferring body fluid to the inner layers of the absorbent system. Apertured co-extruded films such described available on sanitary napkins sold by Johnson & Johnson Inc. of Montreal, Canada could be useful as cover layers in the present invention.

The cover layer 42 may be embossed to the remainder of the absorbent system 44 in order to aid in promoting hydrophilicity by fusing the cover to the next layer. Such fusion may be effected locally, at a plurality of sites or over the entire contact surface of cover layer 42 and absorbent system 44. Alternatively, the cover layer 42 may be attached to the absorbent system 44 by other means such as by adhesion.

Main Body—Absorbent System

The absorbent system 44 may comprise a single layer of material or may comprise multiple layers. In one embodiment, the absorbent system 44 is a blend or mixture of cellulosic fibers and superabsorbent disposed in and amongst fibers of that pulp.

Cellulosic fibers that can be used in the absorbent system 44 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. Flexibility of the material may also be improved by mechanically working the material or tenderizing the material.

The absorbent system 44 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc.

In one preferred embodiment of the invention, the absorbent system consists of fluff pulp and superabsorbent, wherein absorbent system includes between about 3.0 g to about 15.0 g of pulp and more preferably between about 4.0 g to about 5.0 g of pulp, and between about 0.1 g to about 3 g of superabsorbent, and more preferably between about 0.5 g and 1 g of superabsorbent. Preferably the absorbent system in this embodiment has a density of between about 0.04 g/cm$^3$ to about 0.2 g/cm$^3$, and more preferably between about 0.08 g/cm$^3$ and 0.15 g/cm$^3$.

In another preferred embodiment of the invention, the absorbent system consists essentially of fluff pulp and superabsorbent, wherein absorbent system includes between about 3.0 g to about 15.0 g of pulp and more preferably between about 4.0 g to about 5.0 g of pulp, and between about 0.1 g to about 3 g of superabsorbent, and more preferably between about 0.5 g and 1 g of superabsorbent . Preferably the absorbent system in this embodiment has a density of between about 0.04 g/cm$^3$ to about 0.2 g/cm$^3$, and more preferably between about 0.08 g/cm$^3$ and 0.15 g/cm$^3$.

In yet another preferred embodiment of the invention, the absorbent system consists of fluff pulp and superabsorbent, wherein absorbent system includes between about 80% to about 98% by weight of pulp and about 2% to about 20% by weight of superabsorbent, and more preferably between about 8% and about 15% superabsorbent. Preferably the absorbent system has a density of between about 0.04 g/cm$^3$ to about 0.2 g/cm$^3$, and more preferably between about 0.08 g/cm$^3$ and 0.15 g/cm$^3$.

In still another preferred embodiment of the invention, the absorbent system consists essentially of fluff pulp and superabsorbent, wherein absorbent system includes between about 80% to about 98% by weight of pulp and about 2% to about 20% by weight of superabsorbent, and more preferably between about 8% and about 15% of superabsorbent. Preferably the absorbent system in this embodiment has a density of between about 0.04 g/cm$^3$ to about 0.2 g/cm$^3$, and more preferably between about 0.08 g/cm$^3$ and 0.15 g/cm$^3$.

In still another preferred embodiment of the invention, the absorbent system consists essentially of fluff pulp and superabsorbent, wherein absorbent system includes between about 80% to about 98% by weight of pulp and about 2% to about 20% by weight of superabsorbent, and more preferably between about 8% and about 15% of superabsorbent, and the absorbent system does not contain a carrier, bonding fibers, latex adhesives, or other material for bonding the fibers of the absorbent system to one another. Preferably the absorbent system in this embodiment has a density of between about 0.04 g/cm$^3$ to about 0.2 g/cm$^3$, and more preferably between about 0.08 g/cm$^3$ and 0.15 g/cm$^3$.

Main Body—Barrier Layer

Underlying the absorbent layer 44 is a barrier layer 50 comprising liquid-impervious film material so as to prevent liquid that is entrapped in the absorbent system 44 from egressing the sanitary napkin and staining the wearer's undergarment. The barrier layer 50 is preferably made of polymeric film, although it may be made of liquid impervious, air-permeable material such as repellent-treated non-woven or micropore films or foams.

The barrier layer may be breathable, i.e., permits vapor to transpire. Known materials for this purpose include non-woven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 42 and the barrier layer 50 are joined along their marginal portions so as to form an enclosure or flange seal that maintains the absorbent layer 44 captive.

Any or all of the cover, absorbent layer, transfer layer, backsheet layer, and adhesive layers may be colored. Such coloring includes, but is not limited to, white, black, red, yellow, blue, orange, green, violet, and mixtures thereof. Color may be imparted according to the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like. Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

The absorbent article may include other known materials, layers, and additives, such as, foam, net-like material, perfumes, medicaments or pharmaceutical agents, moisturizers, odor control agents, and the like. The absorbent article can optionally be embossed with decorative designs.

The absorbent article may be packaged as unwrapped absorbent articles within a carton, box or bag. The consumer withdraws the ready-to-use article as needed. The absorbent article may also be individually packaged (each absorbent article encased within an overwrap).

Also contemplated by the present invention are asymmetrical and symmetrical absorbent articles having parallel longitudinal edges, dog bone- or peanut-shaped, as well as articles having a tapered construction for use with thong-style undergarments.

Adhesive

The adhesive 33 employed in the present invention may be any pressure sensitive adhesive, and preferably a hot melt adhesive, that possesses the specific rheological properties set forth in further detail below. The rheological analysis of an adhesive is a method of determining the viscoelastic properties polymers. Rheometer devices for determining rheolgocial properties of adhesives are well known to those skilled in the art. For example, a Rheometrics Solids Analayzer II manufactured by Rheometrics Inc., of Piscataway N.J. was used to analyze the adhesives according to the present invention to determine the rheological properties thereof.

It is critical to the present invention that the adhesive 33 have the following properties: (i) a ratio of the Dynamic Shear Storage Modulus (G') measured at 37° C. and 100 radians/s to Dynamic Shear Storage Modulus (G') at 37° C. and 0.1 radians/second that is greater than or equal to 4.5; and (ii) a glass transition temperature Tg between −20° C. and 15° C.

The above described properties can be represented by the following formulas:

$$G'_{[100\ rad/sec@\ 37°\ C.]}/G'_{[0.1\ rad/sec@\ 37°\ C.]} \geq 4.5;\ \text{and}$$

$$-20°\ C. \leq Tg(°\ C.) \leq 15°\ C.$$

The adhesives employed in the present invention preferably have a Tg value of between −20° C. and 15° C., more preferably between −20° C. and 0°, and most preferably between −20° C. and −10° C.

The adhesives employed in the present invention preferably have a $G'_{[100\ rad/sec@\ 37°\ C.]}/G'_{[0.1\ rad/sec@\ 37°\ C.]}$ value of greater than or equal to 4.5, more preferably between 4.5 and 7, and most preferably between 4.8 and 6.

The adhesive 33 employed in the article according to the present invention preferably has more than about 50% by weight of a liquid plasticizer, preferably more than about 65% by weight of a liquid plasticizer, and most preferably more than about 80% by weight of a liquid plasticizer. Suitable liquid plasticizers may include white oils, mineral oils, paraffinic process oils, polyethylene glycol, glycerin, polypropylene glycol, napthenic oils, and liquid polyterpenes. The liquid plasticizer preferably has a molecular weight of less than 1000 g/mole, more preferably less than 750 g/mole and most preferably less than 500 g/mole.

The adhesive 33 used in the article according to the present invention is preferably an adhesive based upon block copolymers, preferably, those which may include linear or radial co-polymer structures having the formula $(A-B)_x$ wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or most preferably hydrogenated elastomers such as ethylene-butylene or ethylene-propylene or polyisobutylene, or combinations thereof, specifically, adhesives consisting of styrene-ethylene-butylene-styrene (SEBS) block copolymer and mineral oils, paraffinic or napthenic process oils, and optionally a suitable tackifying resins include natural and modified resins; glycerol and pentaerythritol esters of natural and modified resins; polyterpene resins; copolymers and terpolymers of natural terpenes; phenolic modified terpene resins and the hydrogenated derivatives thereof; aliphatic petroleum resins and the hydrogenated derivatives thereof; aromatic petroleum resin and the hydrogenated derivatives thereof; and aliphatic/aromatic petroleum resins and the hydrogenated derivatives thereof, and combinations thereof.

Adhesives of the type described above are commercially available from National Starch and Chemical, Bridgewater, N.J. Specific examples of adhesives particularly useful for the present invention include adhesives identified by product codes 95-2(34-548B) and 85-2 (34-547B) commercially available from National Starch and Chemical, Bridgewater, N.J.

Figure 5:
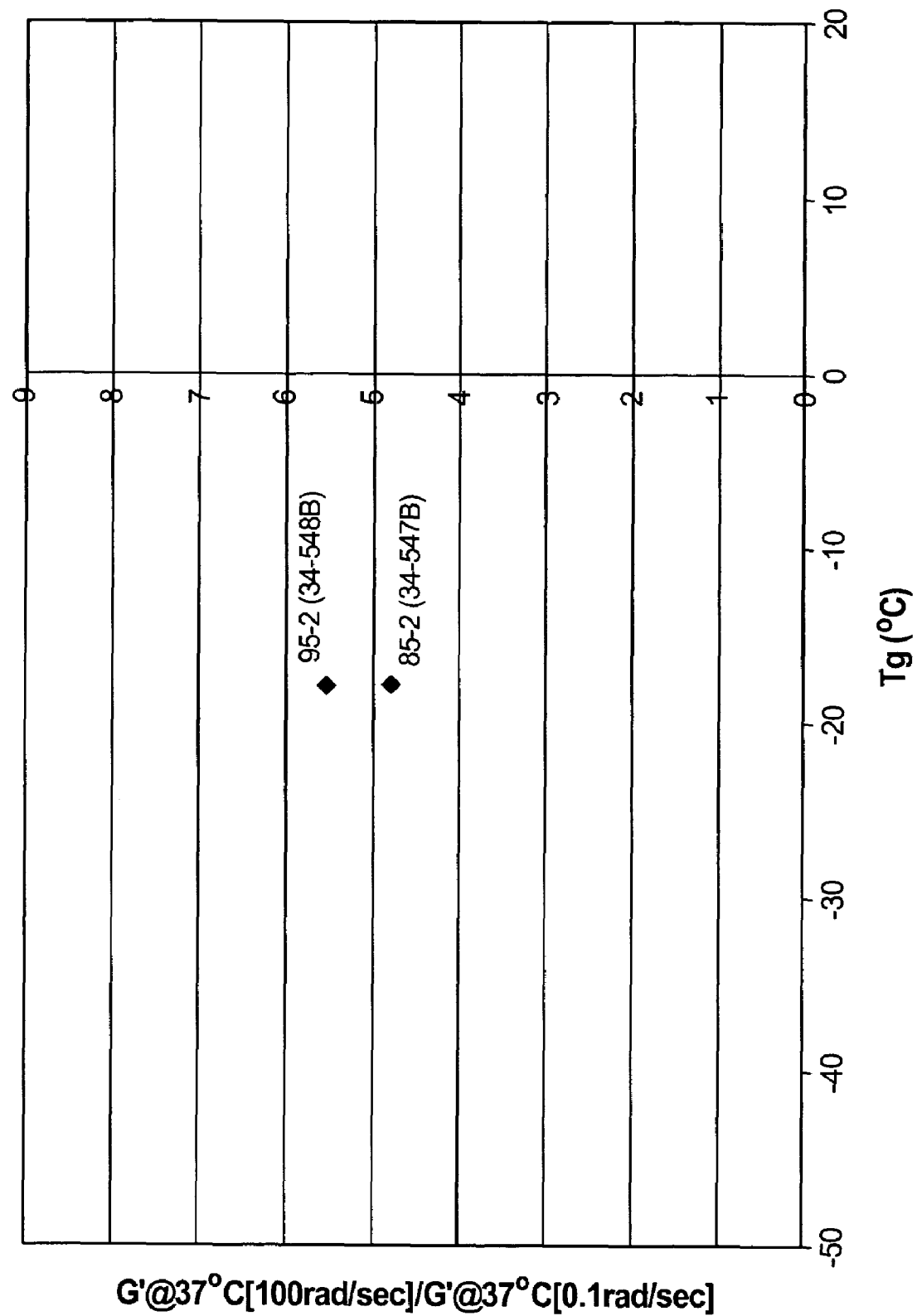
FIG. 5 is a graph of the glass transition temperature Tg (in ° C.) verses the rheological properties $G'_{[100\ rad/sec@\ 37°\ C.]}/G'_{[0.1\ rad/sec@\ 37°\ C.]}$ of adhesives employed in the present invention.

Adhesive 85-2 (34-547B) was measured to have a Tg(° C.) of −18° C. and a $G'_{[100\ rad/sec@\ 37°\ C.]}/G'_{[0.1\ rad/sec@\ 37°\ C.]}$ value of 4.9. Adhesive 95-2 (34-548B) was measured to have a Tg(° C.) of −18° C. and a $G'_{[100\ rad/sec@\ 37°\ C.]}/G'_{[0.1\ rad/sec@\ 37°\ C.]}$ value of 5.5. These properties are shown in the graph of FIG. 5.

EXAMPLE

A specific example of a body-attachable sanitary napkin according to the present invention is described below.

Example #1

A body-attachable sanitary napkin according to the present invention was constructed including a 30 gsm cover nonwoven material commercially available from Polymer Group, Inc., North Charleston, S.C. as product code 65130. The napkin further included an absorbent core arranged below the cover, the absorbent core including (i) 420 gsm calendered fluff pulp, the pulp commercially available from Rayonier, Inc., Atlanta, Ga. as product code Rayfloc JLDE, and (ii) 93 gsm of Aquakeep SA70 superabsorbent, commercially available from Sumitomo Seika Chemicals Co., Ltd. of Osaka, Japan. The fluff pulp portion of the core had an oval shape and measured 180 mm (length)×60 mm (wide). The superabsorbent was applied down the center of the pulp core in a central strip measuring 180 mm×30 mm. The core had a final thickness of 5.3 mm. The napkin contained 3.6 g of pulp and 0.5 g of superabsorbent and the core had a density of 0.13 g/cm³. The napkin further included a 0.9 mil polyethylene film barrier commercially available from Pliant Corporation, Schaumburg, Ill., as product code XP3492B. The cover and barrier were constructed to extend beyond the core such that the product had an oval shape with product dimensions of 240 mm (length)×95 mm (wide). The various layers of the article were adhered to one another using commercially available hot met adhesives such as those available from H.B. Fuller. Adhesive for adhering the article to the body was applied to a body-facing surface of the cover in two 20 mm wide lines spaced 32 mm apart, the adhesive was applied by slot coating directly to the cover in an amount of 55 gsm. The adhesive applied to the body-facing surface of the cover is commercially available as product code 85-2 (34-547B) from National Starch and Chemical, Bridgewater, N.J.

Test Method for Determining Average Removal Force

In order for the absorbent article according to the present invention to securely attach to the body, and remain securely adhered to the body during use, the article must have a sufficient removal force. Absorbent articles according to the present invention will have a removal force in the range of 2.5 g/per mm width of adhesive to 4.5 g/per mm width of adhesive and more preferably between 3.0 g/per mm width of adhesive to 4.0 g/per mm width of adhesive according to the test method set forth in detail below.

The test method for determining average removal force was carried out using a Cheminstruments Ahesion/Release Tester AR1000, available from Cheminstruments, Fairfield Ohio. The test method is set forth in detail below.

(1) A low density polyethylene (LDPE) test plate measuring 3" wide, 6" long and ⅛" thick, was constructed from LDPE commercially available from McMaster-Carr, New Brunswick. The LDPE comes in 48"×48" sheets and was cut to form the LDPE test plate.

(2) The LDPE test plate was secured to the test bed of the apparatus using conventional masking tape.

(3) The product was cut lengthwise using a JDC Precision Sample Cutter, available from Thwing-Albert Instrument Company, Philadelphia, Pa., from a portion of the product containing the body facing adhesive, to obtain a 1" wide product sample, The 1" sample was taken from a product constructed as described in Example #1, the 1" sample was taken at a location so as to include one of the 20 mm wide adhesive lines.

(4) The cut product sample was placed body-facing adhesive side down on the LDPE test plate.

(5) A small masking tape tab of about 1" was applied to one end of the product sample.

(6) A 4.5 pound hand held roller was passed over the product sample to secure it to the test plate, a single forward and back pass was made over the product at a speed of about 12 inches per minute to ensure contact between the sample and the plate. Care should be taken to simply pass the roller over the sample without applying additional manual force. The hand roller is commercially available from Chemsultants International, 9349 Hamilton Drive, Mentor Ohio 44061-1118. The manner of using such hand rollers is well know to those skilled in the art.

(7) The masking tape tab is inserted into the grip of the instrument and clamped.

(8) The instrument is started and the removal force in grams force is recorded.

(9) The above described steps are repeated for nine additional products so that a total of ten products are tested. The average force is calculated and recorded.

(10) Using the calculated average force the average removal force on a per mm width of adhesive basis is determined. The product sample for Example #1 was cut from the product to include a single 20 mm wide adhesive line. Thus, for Example #1, the recorded average force was divided by 20 mm. The calculated average removal force on a per unit of adhesive basis for Example #1 was determined to be 3.42 g/mm width of adhesive.

Removal Pain Test

A removal pain test was utilized to evaluate pain during removal of a sanitary article according to the present invention from the body. Product samples having a construction as described in Example #1 were provided to 30 women. Two (2) product samples were given to each woman. Each of the women were instructed to adhere the product to the body with the center of the product arranged over the vaginal opening. Each of the women were provided the following instructions:

(1) Maximum wear time is four (4) hours;

(2) Product cannot be worn overnight;

(3) Product is for one-time use only, cannot be reworn;

(4) Upon removal of each product, record the "pain upon removal" based upon a 0-10 scale, where 0-1 is no pain, 1-2.5 is no pain but can be felt, 2.5-5.5 is slight pain, 5.5-8.5 is painful, and 8.5-10 is very painful;

(5) A total was determined by adding all the ratings and the average rating was determined by dividing the total by the number of ratings.

The average pain rating for the absorbent article described in Example #1 was 4.0.

In view above, absorbent articles according to the present invention will remain securely in place during use yet will present moderate to low pain to the user upon removal of the article.

From the foregoing description, one skilled in the art can ascertain the essential characteristics of this invention, and without departing from the spirit and scope thereof, can make various changes and modifications. Embodiments set forth by way of illustration are not intended as limitations on the variations possible in practicing the present invention.

I claim:

1. A body-attachable absorbent article comprising:
a body-facing surface;
an adhesive applied to said body-facing surface for selectively securing said article to a body of a user, wherein said adhesive has the following properties:

$$G'_{[100\ rad/sec\ @\ 37°\ C.]}/G'_{[0.1\ rad/sec\ @\ 37°\ C.]} \geq 4.5;\ \text{and}$$

$$-20°\ C. \leq Tg(°\ C.) \leq 15°\ C.$$

2. The absorbent article according to claim 1, wherein said adhesive has a $G'_{[100\ rad/sec\ @\ 37°\ C.]}/G'_{[0.1\ rad/sec\ @\ 37°\ C.]}$ value of between 4.5 and 7.

3. The absorbent article according to claim 2, wherein said adhesive has a $G'_{[100\ rad/sec\ @\ 37°\ C.]}/G'_{[0.1\ rad/sec\ @\ 37°\ C.]}$ value of between 4.8 and 6.

4. The absorbent article according to claim 1, wherein said adhesive has a Tg value of between −20° C. and 15° C.

5. The absorbent article according to claim 4, wherein said adhesive has a Tg value of between −20° C. and 0° C.

6. The absorbent article according to claim 5, wherein said adhesive has a Tg value of between −20° C. and 10° C.

7. The absorbent article according to claim 1, wherein said adhesive is applied to said body facing surface in a plurality of spaced lines.

8. The absorbent article according to claim 7, wherein each of said lines has a width in the range of about 3 mm to about 40 mm.

9. The absorbent article according to claim 8, wherein each of said lines has a width in the range of about 10 mm to about 25 mm.

10. The absorbent article according to claim 7, wherein each of the plurality of spaced adhesive lines are spaced from each other by a distance of between about 3 mm and about 60 mm.

11. The absorbent article according to claim 10, wherein each of the plurality of the plurality of spaced adhesive lines are spaced from each other by a distance of between about 10 mm and about 25 mm.

12. The absorbent article according to claim 7, wherein said adhesive lines are applied to the body facing surface in an amount between about 45 gsm and 100 gsm.

13. The absorbent article according to claim 1, wherein said adhesive is applied substantially over said entire body facing surface in an amount between about 35 gsm and 120 gsm.

14. The absorbent article according to claim 1, wherein said adhesive is applied substantially over said entire body facing surface in an amount between about 45 gsm and 100 gsm.

15. The absorbent article according to claim 1, wherein said article has an average removal force of between about 2.5 g/per mm width of adhesive to about 4.5 g/per mm width of adhesive.

16. The absorbent article according to claim 15, wherein said article has and average removal force of between about 3.0 g/per mm with of adhesive to about 4.0 g/per mm width of adhesive.

17. A body-attachable sanitary napkin comprising:
a cover layer;
a barrier layer;
an absorbent layer arranged between said cover layer and said barrier layer;
an adhesive applied to a body-facing surface of the napkin for selectively securing said article to a body of a user, wherein said adhesive has the following properties:

$$G'_{[100\ rad/sec\ @\ 37°\ C.]}/G'_{[0.1\ rad/sec\ @\ 37°\ C.]} \geq 4.5;\ \text{and}$$

$$-20°\ C. \leq Tg(°\ C.) \leq 15°\ C.$$

18. The body-attachable sanitary napkin according to claim 17, wherein said absorbent layer consists essentially of fluff pulp and superabsorbent.

19. The body-attachable sanitary napkin according to claim 18, wherein said absorbent layer includes between about 3.0 g to about 15.0 g of pulp and about 0.1 g to about 3 g of superabsorbent.

20. The body-attachable sanitary napkin according to claim 19, wherein said absorbent layer includes between about 4.0 g to about 5.0 g of pulp and about 0.5 g to about 1 g of superabsorbent.

21. The body-attachable sanitary napkin according to claim 17, wherein said absorbent layer includes between about 80% to about 98% by weight of pulp and between about 2% to about 20% by weight of superabsorbent.

22. The body attachable sanitary napkin according to claim 21, wherein said absorbent layer includes between about 8% and about 15% by weight of superabsorbent.

23. A body-attachable absorbent article comprising:
a cover layer;
a barrier layer;
an absorbent layer arranged between said cover layer and said barrier layer;
an adhesive applied to a body-facing surface of the napkin for selectively securing said article to a body of a user, wherein said adhesive has the following properties:

$$G'_{[100\ rad/sec\ @\ 37°\ C.]}/G'_{[0.1\ rad/sec\ @\ 37°\ C.]}\ \text{between 4.8 and 6; and}$$

a Tg value between $-20°$ C. and $-10°$ C.;

said article having an average removal force of between 3.0 g/per mm width of adhesive and 4.0 g/mm width of adhesive.

24. The absorbent article according to claim 23, wherein said absorbent layer consists of fluff pulp and superabsorbent.

25. The absorbent article according to claim 24, wherein said absorbent layer does not contain a carrier, binding fibers, latex adhesives, or other material for binding fibers of said absorbent layer to one another.

26. The absorbent article according to claim 24, wherein the absorbent layer has a density of between about 0.04 g/cm$^3$ to about 0.2 g/cm$^3$.

27. The absorbent article according to claim 26, wherein the absorbent layer has a density of between about 0.08 g/cm$^3$ and 0.15 g/cm$^3$.

28. The absorbent article according to claim 23, wherein the absorbent article is one of a sanitary napkin, liner, or adult incontinence article.

* * * * *